US008802116B2

(12) United States Patent
Jorsal

(10) Patent No.: US 8,802,116 B2
(45) Date of Patent: Aug. 12, 2014

(54) POLOXAMER EMULSION PREPARATIONS

(75) Inventor: Steen Boye Jorsal, Mudgeeraba (AU)

(73) Assignee: Novasel Australia Pty. Ltd., Mudgeeraba, Queensland (AU)

( * ) Notice: Subject to any disclaimer, the term of this patent is extended or adjusted under 35 U.S.C. 154(b) by 1097 days.

(21) Appl. No.: 11/085,646

(22) Filed: Mar. 21, 2005

(65) Prior Publication Data

US 2005/0220831 A1 Oct. 6, 2005

Related U.S. Application Data

(63) Continuation of application No. PCT/AU2004/000218, filed on Feb. 20, 2004.

(30) Foreign Application Priority Data

Feb. 27, 2003 (AU) ................................ 2003900887

(51) Int. Cl.
*A61K 8/02* (2006.01)

(52) U.S. Cl.
USPC ...................... 424/401; 424/78.02; 424/78.03

(58) Field of Classification Search
USPC .......................................................... 424/401
See application file for complete search history.

(56) References Cited

U.S. PATENT DOCUMENTS 4,798,846 A * 1/1989 Glen et al. .................... 514/731
5,698,219 A 12/1997 Valdivia et al.
5,952,004 A * 9/1999 Rudnic et al. ................. 424/455
6,019,963 A * 2/2000 Kling et al. .................. 424/76.1
6,022,547 A * 2/2000 Herb et al. .................... 424/401
6,120,794 A * 9/2000 Liu et al. ....................... 424/450
6,316,011 B1 * 11/2001 Ron et al. ...................... 424/401
6,440,437 B1 * 8/2002 Krzysik et al. ................ 424/402
6,464,966 B1 10/2002 Simon ........................ 424/70.12
6,464,989 B2 10/2002 Dillon et al. .................. 424/401
6,464,990 B2 10/2002 Simonnet et al.
2001/0036918 A1 * 11/2001 Hauer et al. ...................... 514/9
2002/0120015 A1 8/2002 Dennis et al. .............. 514/772.3

FOREIGN PATENT DOCUMENTS

CA 1072413 2/1980
CA 2185803 C 7/2006
DE 19723308 6/1997 ........... A61K 31/165
DE 197 23 308 A1 12/1998
DE 10054919 11/2000 ............... A61K 9/10
EP A-1 018 363 7/2000
EP 1018363 3/2001 .............. B01F 17/00
WO WO90/03429 4/1990 ............... C12N 5/00
WO WO 90/03429 A 4/1990
WO WO93/00160 1/1993 ............... B01J 13/00
WO WO-97/38675 10/1997
WO WO 97/38675 10/1997
WO WO98/50005 11/1998 ............... A61K 7/00
WO WO99/22703 5/1999 ............... A61K 7/16
WO WO99/32151 7/1999 ............. A61K 47/10
WO WO99/44584 9/1999 ............. A61K 9/107
WO WO00/51550 9/2000 ............... A61K 7/00
WO WO 00/51550 A 9/2000
WO WO00/71163 11/2000 ............. A61K 47/22
WO WO00/78301 12/2000 ............. A61K 31/05
WO WO 00/78301 A 12/2000
WO WO01/66087 9/2001 ............. A61K 9/113
WO WO 01/66087 A 9/2001
WO WO02/09671 2/2002 ............. A61K 9/107
WO WO 02/09671 A 2/2002
WO WO02/053100 7/2002

OTHER PUBLICATIONS

MSDS for Poloxamer 124.*
Rajakumar, K. Vitamin D, Cod-Liver Oil, Sunlight, and Rickets: A Historical Perspective. 2003. Pediatrics 112(2):132-135.*
Wasan et al. AAPS PharmSci 2002; 4 (4) article 30.*
PCT International Search Report, PCT/AU2004/000218, Mar. 30, 2004.
Supplemental European Search Report dated Apr. 28, 2006.
Examination Report on AU 2009202265 dated Feb. 2011.
Official Action of the Eurasian Patent Office for 200501369/728.
04712958.0 2102—Communication from the European Patent Office dated Feb. 10, 2011.

* cited by examiner

*Primary Examiner* — James Rogers
(74) *Attorney, Agent, or Firm* — Sunstein Kann Murphy & Timbers LLP

(57) ABSTRACT

An emulsion composition comprising: an aqueous component, a non-ionic block copolymer, and an oil wherein the copolymer comprises at least 10% by weight of the composition.

7 Claims, No Drawings

POLOXAMER EMULSION PREPARATIONS

RELATED APPLICATIONS

This application is a continuation of International Application No. PCT/AU04/000218, which was filed on 20 Feb. 2004, which designated the United States and was published in English, and which claims the benefit of Australian Application 2003900887, filed 27 Feb. 2003. The entire teachings of the above applications are incorporated herein by reference.

FIELD OF THE INVENTION

This invention relates to microemulsions and compositions useful in a variety of pharmaceutical and personal care products and applications. In particular, it provides microemulsions and compositions useful for topical and/or mucosal application of water insoluble or sparingly soluble active agents to oesophageal, otic, vaginal, rectal or ophthalmic surfaces or for application to the epidermis of an animal (such as skin in human) and/or to treat disorders and imperfections of the skin. It also provides a method for making the microemulsions and compositions comprising water insoluble or sparingly soluble active agents.

BACKGROUND ART

Many of the active agents in pharmaceutical and cosmetic preparations comprise oils or are immiscible or insoluble in water. It can be difficult to deliver an effective amount of these active agents in order to provide the desired therapeutic effect, due to their lack of water solubility. It is therefore often desirable to provide such agents in water-based compositions (eg. for oral administration, topical application, intravenous injection, intramuscular injection, subcutaneous injection etc). One of the methods for preparing such compositions is to form an emulsion.

An emulsion is a heterogeneous system consisting of at least two immiscible liquids (such as a water phase and an oil phase), one of which is dispersed in the other in the form of droplets, with continuous and discontinuous phases. The discontinuous phase is referred to variously as the dispersed or internal phase, whereas the phase in which the dispersion occurs is referred to as the continuous or external phase. When water is the continuous phase, the emulsion is referred to as oil-in-water (O/W), and when oil is the continuous phase, the emulsion is referred to as water-in-oil (W/O). O/W emulsions are the most frequently used emulsions. However, W/O emulsions are desirable for many applications and would be more extensively used if problems with instability could be overcome.

Macroemulsions are defined as being formed by high shear mixing and normally having particles of 1 micron to 10 microns in size. Such emulsions are difficult to achieve and possess minimal stability, as the oil and water components separate into distinct phases over time. In addition, the droplet size of the macroemulsion increases with time. Various methods have been developed to stabilize such emulsions, such as the addition of additives such as emulsifiers and finely divided solids.

In contrast, microemulsion systems consisting of oil, water, and appropriate emulsifiers can form spontaneously (i.e. form with minimal agitation) and are therefore thermodynamically stable. This level of thermodynamic stability is highly desirable, but seldom achieved. Microemulsion systems theoretically have an infinite shelf life under normal conditions without separating, in contrast to the limited life of macroemulsions. In addition, the size of the droplets in such microemulsions remains constant and is typically less than 150 nm (in general between 10-50 nm) and the microemulsion has very low oil/water interfacial tension.

Emulsions such as microemulsions are important for the development of new and effective active agent delivery systems that allow water insoluble or sparingly soluble active agents to be provided in aqueous solutions appropriate for human use. The preparation of such microemulsions represents a major technological hurdle for pharmaceutical delivery systems as one must choose materials that are biocompatible, non-toxic, clinically acceptable and form stable microemulsions.

Furthermore, many of the known emulsion formulations suffer from an inability to ensure a controlled and prolonged release of the active agent at the desired site as they have a very short retention time at the tissue to which they are applied, due to being readily washed away or degraded. This inability is particularly undesirable, since most biologically active agents must remain at the desired site for a prolonged period in order to be effective.

In view of the above, there is a need to provide emulsion formulations for delivery of active agents that are multipurpose and can be applied to, for example, topical or mucosal tissues. Such emulsions should preferentially have high bioadhesion capability to ensure contact for a prolonged time. Further they should preferentially be able to carry a high amount of active agent to the site of application for a controlled and prolonged release to the desired tissue.

Although stable emulsion preparations have been described, these compositions typically require the use of high temperatures to melt all ingredients of the oil phase to uniformly disperse the particles of one phase through the particles of the other one. Microemulsions are usually formed at temperatures in excess of 75° C., typically about 90° C., and the composition is then cooled slowly over a period of hours or days to room temperature in order to create the emulsion. For large batches this is a costly and time consuming procedure. There is also the risk that the emulsions will be overheated resulting, for example, in the degradation of some of the ingredients.

Another method by which stable emulsions may be prepared is via the use of surfactants or emulsifiers. Typically, surfactants and emulsifiers for the preparation of emulsions are selected from the group consisting of hydrophilic surfactants and mixtures thereof. To function as a surfactant, a compound must necessarily include polar or charged hydrophilic moieties as well as non-polar lipophilic (hydrophobic) moieties; that is, a surfactant compound must be amphiphilic. An empirical parameter commonly used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. It should be appreciated that the HLB value of a surfactant is merely a rough guide generally used to enable formulation of industrial, pharmaceutical and cosmetic emulsions.

A group of compounds that have been successfully used as surfactants in the production of macro- and microemulsions are the block copolymers of ethylene oxide and propylene oxide, the poloxamers. A number of these compounds have the unusual property that they become liquid when chilled, but harden when warmed, a characteristic known as thermo-reversibility. Such thermo-reversibility is useful in pharmaceutical compounding wherever it is desirable to handle a material in a fluid state, but performance is preferably in a gelled or more viscous state. Such compounds can be drawn into a syringe for accurate dose measurement or easily applied from a bottle or squirted from a dispenser when cold. When the poloxamer warms to body temperature (eg. when applied to skin or mucosal surfaces) it thickens to a suitable consistency to facilitate proper inunction and adhesion.

The desired gelling temperature can be regulated by adjusting the concentration of the block copolymer, with the lower copolymer concentrations giving higher gelling temperatures. Concentrations of the copolymer of at least 18% to 20% by weight are needed to produce a composition which exhibits such a transition at commercially or physiologically useful temperatures. However, it has been found that incorporating high concentrations of copolymer causes the composition to become extremely viscous or "gelatinised" and solutions containing 18% to 20% by weight of poloxamer typically have high viscosity even in the "liquid" phase, so that these solutions can not function under conditions where low viscosity, free-flowing is required prior to transition. For this reason, typical copolymer emulsions usually contain less than 10% copolymer.

Active Agents

Active agents are chemical materials or compounds which, when administered to an organism (human or animal, generally human) induce a desired pharmacologic effect. Many of the active agents in pharmaceutical and cosmetic preparations comprise oils or are immiscible or insoluble in water. An example of such an active agent is Tea Tree Oil (TTO).

TTO is isolated by distilling the oil from the stems and leaves of the paperbark tree *Melaleuca alternafolia*. TTO has medicinal properties including antimicrobial, antiviral, anti-inflammatory and antifungal characteristics. Additionally, TTO provides a soothing sensation when in contact with a person's skin. However, the properties of TTO can only be exploited by formulating delivery systems suitable to the various conditions required. When TTO products, in the form of aqueous creams, are exposed to air, the TTO component oxidates and some of the chemical components can change their characteristics, affecting the medicament's effectiveness and safety. The presence of many of the emulsifying agents used to solubilize TTO in water also inhibit or inactivate the activity of TTO. As a gel suspension, TTO tends to separate from the gel base formula, particularly when the suspension contains concentrations of TTO higher than 2%, a process accentuated by changes in temperature (eg. temperatures over 30° C.) and/or applying physical shear forces, such as kneading the gel suspension.

To deliver an effective amount of TTO, it is desirable to apply the oil in a form that will both remain in contact with the skin for an extended period of time and deliver the highest concentration of TTO possible. Microemulsion formulations are therefore highly desirable as they are thermodynamically stable.

This invention has as its objective the formation of safe and effective pharmaceutical microemulsion delivery systems that can be manufactured without the need for the high temperature preparation. Other aims and aspects of the present invention will be apparent from the following description of the present invention.

SUMMARY OF THE INVENTION

According to the present invention there is provided a composition or more specifically a microemulsion for delivery of water-insoluble active agents, comprising: an aqueous component and a non-ionic block copolymer, and at least an oil that is the active agent or has a water-insoluble active agent dissolved therein.

In the present invention, the term "emulsion" includes both macroemulsions and microemulsions.

Compositions of the present invention will desirably possess bioadhesive or mucoadhesive properties. Preferentially, the composition will be in the form of a liquid or a gel. Most preferably, the microemulsion composition will exist as a gel or will be a liquid that is capable of gelatinising upon contact with dermal or mucosal tissue.

According to a second embodiment, the invention provides a microemulsion or a composition for delivery of water-insoluble active agents, comprising an aqueous component and a non-ionic block copolymer, a hydrophilic, non-ionic short chain fatty acid emulsifier, and at least a oil that is the active agent or has a water-insoluble active agent dissolved therein.

According to a third embodiment, the invention provides a method for preparing the microemulsion composition, comprising the steps of:

(a) Mixing a copolymer with an aqueous solution at a suitable temperature to substantially dissolve the copolymer in the aqueous solution; and (b) Mixing, at cold temperature, an oil that is the active agent or has a water-insoluble active agent dissolved therein, with the aqueous copolymer solution prepared in step (a) to form a microemulsion.

According to a fourth embodiment, the invention provides a method for preparing the microemulsion composition, comprising the steps of:

(a) Mixing a copolymer with an aqueous solution at a suitable temperature to substantially dissolve the copolymer in the aqueous solution;

(b) Mixing a hydrophilic, non-ionic short chain fatty acid emulsifier with an oil that is the active agent or has a water-insoluble active agent dissolved therein, at a low temperature to form an oil mixture; and (c) Mixing the solution prepared in step (a) with the solution prepared in step (b) at a low temperature to form a microemulsion.

Also provided herein are microemulsion compositions formed by the above methods.

Composition of the invention will have a wide variety of applications. When applied topically to the dermal layer of an animal the compositions may include agents to promote bodily attractiveness or to mask the physical manifestations of a disorder or disease, in lieu or in addition to the treatment of a physical disorder. The same agent may have either a cosmetic or pharmaceutical effect, depending upon the amounts used and the manner of administration.

In another aspect of the invention, compositions of the invention may be incorporated into other compositions to impart thickening properties to the final composition. Such thickening properties include enhanced overall viscosity, as well as a desirable viscosity response with temperature. The composition may be useful as a thickener in pH ranges where other thickeners are not effective.

In addition, compositions of the invention may be incorporated into other compositions to impart emolliency to the composition. In this respect the composition may also act as a film-forming bioactive agent after it has been applied to the skin or other mucosal membrane. This film-forming bioactive agent may be used as a barrier to prevent water loss from the skin while treating biological challenges.

Other aspects and advantages of the invention will become apparent to those skilled in the art from a review of the ensuing description.

DETAILED DESCRIPTION OF THE INVENTION

General

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Description of the Preferred Embodiment

The present invention provides a microemulsion composition comprising at least 10% by weight of a copolymer that preferentially has thermo-reversible properties. Copolymer levels of this magnitude exceed, to the best of the applicant's knowledge, those found in other oil-copolymer based microemulsion. When the copolymer used in the microemulsion is thermo-reversible, oil-copolymer combinations may be prepared at a cold temperature. The applicant has found, however, that the combination of an emulsifier with the oil before addition of the copolymer surprisingly allows the microemulsion to be prepared at a low temperature.

According to the present invention there is provided a composition or more specifically a microemulsion for delivery of water-insoluble active agents, comprising: an aqueous component and a non-ionic block copolymer, and at least an oil that is the active agent or has a water-insoluble active agent dissolved therein.

Microemulsions as described herein will comprise an amount by weight of block copolymer of about 10% to about 50% by weight, more preferably the amount by weight block copolymer will be between about 10.1% and 40% by weight of the emulsion while an amount by weight of the block copolymer between any of the following ranges will be highly desirable: 10.5% to 35%, 11% to 30%, 12% to 25%, 13% to 20% or 14% to 18% by weight of the emulsion. Thus, as an illustration of the invention, the block copolymer may comprise 15% by weight of the emulsion.

In addition to the block copolymer being present in the aforementioned weight ranges in the microemulsion, it will also desirably be a thermo-reversible copolymer.

In a preferred embodiment of the invention, the microemulsion or composition will possess bioadhesive or mucoadhesive properties. Such properties will be consistent with the microemulsion or composition being prepared in either a liquid or more preferably a gel form. When prepared in this manner the microemulsion or composition will be useful for topical and/or mucosal application of water insoluble or sparingly soluble active agents to oesophageal, otic, vaginal, rectal or ophthalmic surfaces, or for application to the epidermis of an animal (such as skin in human) and/or to treat disorders and imperfections of the skin. Desirably, the microemulsion or composition will either exist as a gel or will be prepared in such a manner that it is capable of gelatinising upon contact with dermal or mucosal tissue.

When preparing a microemulsion in accordance with the first embodiment of the invention, ideally, the oil and the thermo-reversible copolymer will be mixed at a cold temperature. When this is done at a cold temperature at the weight ranges specified herein the composition forms a stable microemulsion capable of application to dermal or mucosal tissue.

In a second embodiment, the invention provides a composition or more specifically a microemulsion for delivery of water-insoluble active agents, comprising: an aqueous component and a non-ionic block copolymer, a hydrophilic nonionic short chain fatty acid emulsifier and at least an oil that is the active agent or has a water-insoluble active agent dissolved therein.

When preparing a microemulsion in accordance with the second embodiment of the invention, ideally, the oil and the emulsifier will be mixed and then applied to the thermoreversible copolymer. When this is done at a low temperature at the weight ranges specified herein the composition rapidly forms a stable microemulsion capable of application to dermal or mucosal tissue.

The copolymer for use in the present invention is preferably a block copolymer of ethylene oxide and propylene oxide (poloxamer) preferably those represented by the formula:

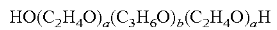

$$HO(C_2H_4O)_a(C_3H_6O)_b(C_2H_4O)_aH$$

Where 'b' is between 15 and 67 and 'a' is between 2 and 130, and the total proportion of 'a' units amounts to from 20% to 90% by weight of the poloxamer. The molecular weight of the poloxamer ranges from preferably about 1,000 to 20,000 and it will preferentially have thermo-reversible properties. By way of example only the block copolymer may be poloxamer 407, such as that sold as Pluronic® F127 (BASF Corporation) or Synperonic PE/F127 (Uniqema).

According to the invention the preferred emulsifier is a fatty acid component with a polyethoxylated side chain. For example, suitable emulsifiers might be Laureth-4, Laureth-9, Laureth-23, PPG-26-Buteth-26/PEG-40 Hydrogenated castor oil or PEG-40 Hydrogenated castor oil. When such emulsifiers are used in the invention the amount by weight of the emulsifier will vary generally from about 0.5% to about 50% by weight of the microemulsion.

The physico-chemical characteristics of the present invention make the microemulsion suitable as a delivery vehicle for water insoluble or sparingly soluble active agents. It is particularly well-suited for transdermal or transmucosal delivery. In this respect the oil phase may comprise oils commonly used in the food, cosmetic and pharmaceutical industries for example, oils of natural or synthetic origin, long chain alcohols, glyceryl esters of fatty acids or fatty esters of monohydric alcohols. The esters and alcohols can be straight or branch chained, saturated or unsaturated and liquids at room temperature. The oil phase may also contain active agents that are soluble in or miscible with the oil phase.

The oil of the present invention may have inherent pharmaceutical properties and constitute the active agent of the microemulsion and/or may contain dissolved active agents that are soluble or miscible in the oil. The active agents may include, but are not limited to, antimicrobials (such as antibiotics, antifungals and antivirals), anti-inflammatories, antihistaminics, antidepressants, anaesthetics antineoplastics, enzymes, cardiovascular agents, polynucleotides, genetic material, viral vectors, immunoactive agents, imaging agents, immunosuppressive agents, peptides, proteins etc and combinations thereof. Pharmaceutically effective amounts of the selected active agents may be determined using techniques well known in the art.

Preferentially the amount by weight of the oil used in the microemulsion will comprise from about 0.1% to about 80% by weight of the emulsion, more preferably 1% to 30% by weight of the emulsion, with a range of 3% to 15% by weight of the emulsion being highly desirable. In an illustration of the invention the oil will constitute about 6% of the total weight of the emulsion.

In a highly preferred form of the invention the oil is tea tree oil (TTO). Where the active agent is TTO the microemulsion will have microbicide activity. Such a composition can be used to treat for example; diseases such as sexually transmitted disease (eg. HIV) by vaginal delivery; impetigo and cold sores by topical preparation, elimination of MRSAs by intranasal application and diseases such as otitis media, otitis externa, acne, periodontitis, gingivitis, paronychia, onychomycosis and secondary infections in connection with operations, dermatitis, burns, etc.

According to a third embodiment, the invention provides a method for preparing the microemulsion composition, comprising the steps of:

(a) Mixing a copolymer with an aqueous solution at a suitable temperature to substantially dissolve the copolymer in the aqueous solution; and (b) Mixing, at cold temperature, an oil that is the active agent or has a water-insoluble active agent dissolved therein, with the aqueous copolymer solution prepared in step (a) to form a microemulsion.

According to step (a) in the method the co-polymer is mixed with an aqueous solution at a suitable temperature to substantially dissolve the copolymer in the aqueous solution. Dissolution of the co-polymer with an aqueous solution will occur almost instantaneously at temperatures of around 6° C. Alternatively, the co-polymer may be mixed with the aqueous solution at room temperature if left over night with semi-continuous or continuous stirring.

As used herein "cold temperature" refers to temperatures less than about 15° C., preferably from about 4° C. to about 12° C. and most preferably less than about 10° C.

According to a fourth embodiment, the invention provides a method for preparing the microemulsion composition, comprising the steps of:

(a) Mixing a copolymer with an aqueous solution at a suitable temperature to substantially dissolve the copolymer in the aqueous solution;

(b) Mixing a hydrophilic, non-ionic short chain fatty acid emulsifier with an oil that is the active agent or has a water-insoluble active agent dissolved therein, at a low temperature to form an oil mixture; and (c) Mixing the solution prepared in step (a) with the solution prepared in step (b) at a low temperature to form a microemulsion.

As used herein "Low temperature" refers to temperatures less than about 60° C., preferably from about 15° C. to about 40° C., more preferably from about 20° C. to about 30° C. and most preferably at about room temperature. The ability to manufacture microemulsions of the present invention at these temperatures is highly significant as it provides a distinguishing feature from most other methods of manufacture of microemulsions which demand the microemulsions be made at about 90° C.

It has been found that a microemulsion composition prepared according to the present invention has the surprising feature that the addition of the oil/emulsifier mixture to the aqueous poloxamer solution at room temperature changes the thermo-reversible nature of the poloxamer by altering the temperature at which solidification occurs. This effect is most evident at high ratios of poloxamer to oil.

Microemulsion compositions of the present invention provide clear, colourless gels that are particularly well suited to pharmaceutic and personal care applications. For example, very little residue is formed upon dehydration, which may be important in some applications, such as in optically applied pharmaceutics. An additional advantage of the microemulsion composition of the invention is that they remain clear and translucent before and after the triggering environmental change. These characteristics of the reversibly gelling microemulsion composition make it well suited for use in pharmaceutic compositions.

The practical advantage of this behaviour of the microemulsion composition is that the formulation can be administered as a flowing liquid at ambient temperatures. Upon contact with body tissues it viscosifies, thus changing its flow properties, and more importantly, its clearance from the site of application is dramatically reduced.

Those skilled in the art will appreciate that microemulsion composition of the present invention may be utilized for a wide variety of pharmaceutic and personal care applications. To prepare a pharmaceutic composition, an effective amount of pharmaceutically active agent(s) which imparts the desirable pharmaceutic effect is incorporated into the reversibly gelling composition of the present invention.

When prepared according to the method of the invention the microemulsion composition can further include one or more pharmaceutically acceptable additives, excipients carriers and diluents. Such additives, excipients carriers and diluents include, without limitation, water, saline, ethanol, dextrose, glycerol, lactose, dextrose, sucrose sorbitol, mannitol, starches, gum acacia, calcium phosphates, alginate, tragacanth, gelatine, calcium silicate, microcrystalline cellulose, polyvinylpyrrolidone, cellulose, water syrup, methyl cellulose, methyl and propylhydroxybenzoates, talc, magnesium stearate and mineral oil or combinations thereof. The formulations can additionally include lubricating agents, pH buffering agents, wetting agents, emulsifying and suspending agents, preserving agents, sweetening agents or flavouring agents, antifoaming agents, polymers, antioxidants, chelating agents, viscomodulators, tonicifiers, flavorants, colorants, odorants, opacifiers, suspending agents, binders, fillers, plasticizers, lubricants, and mixtures thereof. The particular selection of constituent that can be included in the compositions described herein will generally depend on the type of preparation.

In addition, an acid or a base may be incorporated into the microemulsion composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminium hydroxide, calcium carbonate, magnesium hydroxide, magnesium aluminium silicate, synthetic aluminium silicate, synthetic hydrocalcite, magnesium aluminium hydroxide, diisopropylethylamine, ethanolamine, ethylenediamine, triethanolamine, triethylamine, triisopropanolamine, trimethylamine, tris (hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Preferred cations include sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

When the hydrophilic active agent is subject to enzymatic degradation, the present compositions can also include an enzyme inhibiting agent. Enzyme inhibiting agents are shown for example, in Bernskop-Schnurch (1998), "The use of inhibitory agents to overcome enzymatic barrier to perorally administered therapeutic peptides and proteins," *Controlled Release* 52: 1-16.

Generally, inhibitory agents can be divided into the following classes: inhibitors that are not based on amino acids (such as P-aminobenzamidine, FK448, camostat mesylate and sodium glycocholate); amino acids and modified amino acids (such as aminoboronic acid derivatives and n-acetylcysteine); peptides and modified peptides (such as bacitracin, phosphinic acid dipeptide derivatives, pepstatin, antipain, leupeptin, chymostatin, elastatin, bestatin, hosphoramindon, puromycin, cytochalasin potatocarboxy peptidase inhibitor, and amastatin); polypeptide protease inhibitors (such as aprotinin, Bowman-Birk inhibitor, soybean trypsin inhibitor, chicken egg white trypsin inhibitor, chicken ovoinhibitor, and human pancreatic trypsin inhibitor); complexing agents (such as EDTA, EGTA, 1,10-phenanthroline and hydroxychinoline); and mucoadhesive polymers and polymer-inhibitor conjugates (such as polyacrylate derivatives, chitosan, cellulosics, chitosan-EDTA, chitosan-EDTA-antipain, polyacrylic acid-bacitracin, carboxymethyl cellulose-pepstatin and polyacrylic acid-Bowman-Birk inhibitor). The choice and levels of the enzyme inhibitor are based on toxicity, specificity of the proteases and the potency of inhibition.

A discussion of particular applications and formulations follows.

Esophageal, oral cavity and buccal applications: One indication for the use of this microemulsion composition would be to provide a suitable vehicle for delivering a pharmaceutic effect within the oesophageal lining. In this respect the mucoadhesive properties of the microemulsion composition of the invention make that composition desirable for controlling and facilitating a pharmaceutic effect to the oesophageal lining. The shear sensitivity of the microemulsion composition could also be taken advantage of in applications in which a liquid treatments is sprayed under high shear conditions onto the oral cavity, where the solution adheres and viscosifies to provide a reservoir for antibacterial agents, such as chlorohexadine, or a breath freshener.

Ophthalmic applications: Most ophthalmic drugs are applied to the eye, typically to the precorneal area. The most common dosage form is a liquid drop. Drug bioavailability is generally low because liquid formulations are quickly cleared from the eye by tearing and blinking, resulting in the need for frequent dosing and uneven drug delivery.

The microemulsion composition described herein provides a new vehicle for achieving greater bioavailability of topically administered insoluble or partially soluble ophthalmic active agents. Formulations containing such active agents can be applied as drops that viscosify or gel upon contact with eye. Since gelling can be accomplished with low concentrations of the polymer, blurring can be minimized upon drop instillation.

When used in this manner the microemulsion composition would preferentially be used for delivering bioactive materials, such as anaesthetics, mydriatics and cycloplegics, antimicrobial agents (antibacterial, antifungal, antiviral), anti-inflammatory agents, agents for the treatment of glaucoma, ocular decongestants, diagnostic agents, and wound healing agents.

Nasal applications: Microemulsion compositions of the invention may also be used for delivery of drugs to the nasal cavity. Nasal drug delivery has been considered as an alternative to parenteral routes of administration of drugs that demonstrate low oral bioavailability. In order to increase the bioavailability of nasally administered drugs, efforts have been made to increase the residence time of formulations in the nasal cavity. Nasal delivery of drugs can offer advantages over other methods of delivery, including rapid systemic absorption, lower dosing, more rapid onset of desired therapeutic effects, and improved pharmacokinetics. In addition, it provides an alternative route for administering peptide drugs, which generally have low bioavailability via the oral route and are normally administered parenterally.

Microemulsion composition would potentially be useful for delivering agents such as decongestants, antihistamines, anti-osteoporosis agents, hormones, antineoplastic agents, Parkinsonism drugs, etc. The composition may also be used for the application of vaccines, such as those against the influenza virus.

Vaginal/rectal applications: Microemulsion compositions of the invention are also indicated for the delivery of bioactive agents (such as TTO) to the vaginal or the rectal cavity. These delivery routes have been considered as an alternative to parenteral routes of administration of bioactive agents that demonstrate low oral bioavailability. In order to increase the bioavailability of vaginally or rectally administered bioactive agents, efforts have been made to increase the residence time of formulations in these cavities. These routes offer advantages over other methods of delivery, including rapid systemic absorption, lower dosing, more rapid onset of desired therapeutic effects, and improved pharmacokinetics.

Veterinary applications: Microemulsion compositions of the invention may also be useful in the treatment of not only human conditions but in providing treatments for animal care. For veterinary products, the microemulsion compositions is indicated for the preparation of topical dermal products, such as antibacterials, antifungals, antipruritics, and antiseborrheia, antiodor, and antiseptic/wound healing preparations. Otic products would include ear cleaners with or without actives, such as, antifungals. Ophthalmic products would include eye moisturizers or antimicrobial preparations.

Personal Care Applications: Microemulsion compositions of the invention may also be particularly well suited for cosmetic applications. For example, very little residue is formed upon dehydration, which may be important in some applications, such as in topically applied cosmetics. An additional advantage of the composition of the invention is that it remains clear and translucent above and below the critical temperature or pH. These characteristics of the microemulsion compositions make it well suited for use in cosmetic compositions.

To prepare a cosmetic composition, an effective amount of cosmetically active agent(s) that imparts the desirable cosmetic effect is incorporated into the microemulsion composition of the present invention. Preferably the selected agent lends itself to a homogeneous dispersion through out the microemulsion composition. It is contemplated as within the scope of the invention that the reversibly gelling composition compositions of the present invention may be prepared under sterile conditions.

Exemplary cosmetic and personal care applications, in which the microemulsion composition may be used include, but are not limited to, baby products, bath preparations, eye makeup preparations, fragrance preparations, noncolouring hair preparations, colour cosmetics, hair colouring preparations, makeup preparations, manicuring preparations, oral hygiene products, shaving preparations, skin care preparations, and suntan preparations such as suntan creams, gels and lotions, indoor tanning preparations.

The cosmetic composition may be in any form. Suitable forms include but are not limited to lotions, creams, sticks, roll-ons formulations, mousses, aerosol sprays, pad-applied formulations, and film-forming formulations.

Preparation of the above-named cosmetic compositions and others may be accomplished with reference to any of the cosmetic formulation guidebooks and industry journals which are available in the cosmetic industry. These references supply standard formulations which may be modified by the addition or substitution of the microemulsion composition of the present invention into the formulation. Suitable guidebooks include Cosmetics and Toiletries Magazine, Vol. 111 (March, 1996); Formulary: Ideas for Personal Care; Croda, Inc, Parsippany, N.J. (1993); and Cosmeticon: Cosmetic Formulary, BASF, which are hereby incorporated in their entirety by reference.

Preparation of pharmaceutic compositions may be accomplished with reference to any of the pharmaceutic formulation guidebooks and industry journals which are available in the pharmaceutic industry. These references supply standard formulations which may be modified by the addition or substitution of the microemulsion compositions of the present invention. Suitable guidebooks include Pharmaceutics and Toiletries Magazine, Vol. 111 (March, 1996); Formulary: Ideas for Personal Care; Croda, Inc, Parsippany, N.J. (1993); and Pharmaceuticon: Pharmaceutic Formulary, BASF, which are hereby incorporated in their entirety by reference.

Exemplary drugs or therapeutics delivery systems which may be administered using the aqueous responsive compositions of the invention include, but are in no way limited to, mucosal therapies, such as esophageal, otic, rectal, buccal, oral, vaginal, and urological applications; topical therapies, such as wound care, skin care and teat dips; and intravenous/subcutaneous therapies, such as intramuscular, intrabone (e.g., joints), spinal and subcutaneous therapies, tissue supplementation, adhesion prevention and parenteral drug delivery.

The term “animal” used herein is taken to mean mammals, such as primates, including humans, sheep, horses, cattle, pigs, dogs, cats, rats, mice; it also includes, birds, reptiles, and fish.

As will be understood by those skilled in the art, two or more pharmaceutical agents may be combined for specific effects. The necessary amounts of active ingredient can be determined by simple experimentation.

The invention is now described with reference to the following examples which are presented for the purpose of illustration only and are not limiting of the invention.

Best Mode(s) for Carrying Out the Invention

Example 1

Manufacture of Vaginal Gel B

Part A

Add 15.6 g Lutrole F127 to 84.4 g deionised water, which is held at a temperature of 6° C. Combine with slow mixing to reduce air entrapment and place under vacuum for a few minutes to remove any trapped air after Lutrol® F127 is dissolved.

Part B

Add 0.20 g fumaric acid to 5.0 g alcohol by stirring until dissolved. Cool the solution to 10° C.

Part C

Combine 3.0 g Tea Tree oil, 5.0 g propylene glycol and 2.0 g undecylenic acid and mix to dissolve all ingredients. Cool the solution to 10° C.

Gel Preparation

Place 84.8 g of the Lutrol® F127 solution of Part A in a vessel and hold at 10° C. Slowly add 5.2 g of the fumaric acid solution of Part B and mix well, maintaining the solution at 10° C. Slowly add 10.0 g of the Tea Tree oil solution of Part C with gentle stirring and whilst maintaining the solution at 10° C. If necessary, remove any aeration by placing the gel under vacuum. Allow the gel to warm to room temperature.

Example 2

Manufacture of Poloxamer Gel 8C

Part A

Heat 76.3 g deionised water to 60-65° C., slowly add 16.7 g poloxamer 407 and stir gently for approximately 2 hours or until all the poloxamer is dissolved and the solution thickens. Allow the solution to cool to room temperature and leave overnight. Adjust the pH of the solution to 4.2-5.0 with potassium hydroxide.

Part B

Combine 3.0 g of PPG-26-Buteth-26/PEG-40 Hydrogenated castor oil, 3.0 g Tea Tree oil and 1.0 g d-alpha tocopheryl acetate with gentle mixing.

Gel Preparation

Add 7.0 g of the Tea Tree oil solution of Part B to 93.0 g of the room temperature poloxamer solution of Part A. Mix with gentle stirring until the solution thickens.

Example 3

Manufacture of Poloxamer Gel 8E

Part A

Heat 73.4 g deionised water to 60-65° C., slowly add 16.0 g poloxamer 407 and stir gently for approximately 2 hours or until all the poloxamer is dissolved and the solution thickens. Allow the solution to cool to room temperature and leave overnight. Adjust the pH of the solution to 4.2-5.0 with potassium hydroxide.

Part B

Combine 2.0 g Laureth4, 1.0 g of Laureth-23, 6.0 g Tea Tree oil and 1.0 g d-alpha tocopheryl acetate, 0.1 g of 1.0 M (1 U/g) retinyl palmitate and 0.5 g panthenol. Heat solution to 40-45° C. with gentle mixing to dissolve all components.

Gel Preparation

Add 10.6 g of the Tea Tree oil solution of Part B to 89.4 g of the room temperature poloxamer solution of Part A. Mix with gentle stirring until the solution thickens.

Example 4

Testing of Gel Formulations Against Microorganisms

The products were tested using macrodilution and microdilution methods, using a 96-well microtitre tray. The highest concentration of gel tested was 50% product.

The test organisms were *Staphylococcus aureus* NCTC 6571, *Escherichia coli* NCTC 10418, *Pseudomonas aeniginosa* NCTC 10662 and the yeast *Candida albicans* ATCC 10231.

Inocula were prepared in double strength Mueller Hinton broth, resulting in a final concentration of single strength broth and organisms at a final concentration of approximately $5\times10^5$ cfu/mL. Tests were incubated at 37° C. for 24 hours. After this time, trays were subcultured by removing 5 μL from tray wells and spot inoculating onto Mueller Hinton agar. All subcultures were incubated for 24 hours and the colonies counted.

The minimum inhibitory concentration (MIC) was defined as the lowest concentration of product resulting in the maintenance or reduction of the inoculum. The minimum cidal concentration (MCC) was defined as the lowest concentration of product resulting in the death of 99.9% of the inoculum.

| | | MIC/MCC | | | |
|---|---|---|---|---|---|
| Product | TTO % | *C. albicans* | *S. aureus* | *E. coli* | *P. aeruginosa* |
| Vaginal gel B | 3.0 | <0.78/<0.78 | <2.1/<2.1 | 4.2/4.2 | 33.0/33.0 |
| Poloxamer gel 8C | 3.0 | — | >1.5/>1.5 | — | >1.5/>1.5 |
| Poloxamer gel 8E | 6.0 | 0.38/0.38 | 0.75/0.75 | <0.19/<0.19 | >3.0/>3.0 |

The invention claimed is:

1. A topical or mucosal microemulsion composition suitable for pharmaceutical or cosmetic applications, comprising:

(a) an aqueous component;

(b) a non-ionic block copolymer of ethylene oxide and propylene oxide;

(c) a tea tree oil present in an amount of about 3% to 15% by weight of the microemulsion; and (d) a hydrophilic fatty acid emulsifier with a polyethoxylated side chain;

wherein: (i) the copolymer is a flowing liquid at ambient temperatures, (ii) the tea tree oil is present in an effective amount to impart a pharmaceutical or cosmetic effect of the composition, (iii) the microemulsion is thermoreversible and gelatinises or viscosifies upon contact with dermal, ophthalmic or mucosal tissue to develop bioadhesive or mucoadhesive properties, iv) the microemulsion composition comprises an amount by weight of said non-ionic block copolymer of 10% to 50% by weight, and (v) the non-ionic block copolymer of ethylene oxide and propylene oxide is poloxamer 407.

2. A microemulsion composition suitable-for topical or mucosal applications, comprising:

(a) an aqueous component;

(b) a non-ionic block copolymer of ethylene oxide and propylene oxide;

(c) a tea tree oil present in an amount of about 3% to 15% by weight of the microemulsion; and (d) a hydrophilic fatty acid emulsifier with a polyethoxylated side chain;

wherein (i) the composition is prepared as a liquid, (ii) the composition is thermoreversible, (iii) the composition gelatinises upon contact with dermal or mucosal tissue, (iv) the composition possesses bioadhesive or mucoadhesive properties v) the microemulsion composition comprises an amount by weight of said non-ionic block copolymer of 10% to 50% by weight, and (vi) the nonionic block copolymer of ethylene oxide and propylene oxide is poloxamer 407.

3. The composition of claim 1 or 2, wherein the copolymer comprises at least 18 to 20% by weight of the microemulsion.

4. A topical or mucosal microemulsion composition suitable for pharmaceutical or cosmetic applications, comprising:

(a) an aqueous component;

(b) a non-ionic block thermoreversible copolymer of ethylene oxide and a propylene oxide present in an amount of about 10 to 50% by weight of the microemulsion;

(c) a hydrophilic fatty acid emulsifier with a polyethoxylated side chain present in an amount of about 0.5 to 50% by weight of the microemulsion; and (d) a tea tree oil present in an amount of about 3 to 15% by weight of the microemulsion;

wherein: (i) the tea tree oil is present in an effective amount to impart a pharmaceutical or a cosmetic effect to the composition, (ii) the microemulsion is thermoreversible and gelatinises or viscosifies upon contact with dermal, ophthalmic or mucosal tissue to develop bioadhesive or mucoadhesive properties and (iii) the non-ionic block copolymer of ethylene oxide and propylene oxide is poloxamer 407.

5. The microemulsion composition of claim 4 wherein the copolymer comprises at least 18 to 20% by weight of the microemulsion.

6. The microemulsion composition of any one of claims 1, 2 or 4, wherein the oil and copolymer are mixed at a temperature of less than 60° C.

7. A topical or mucosal microemulsion composition for pharmaceutical or cosmetic applications, comprising:

(a) an aqueous component;

(b) a non-ionic block copolymer of ethylene oxide and propylene oxide present in an amount of 10.5% to 35% by weight of the microemulsion;

(c) a hydrophilic fatty acid emulsifier with a polyethoxylated side chain present in an amount of about 0.5 to 50% by weight of the microemulsion; and (d) a tea tree oil present in an amount of about 3 to 15% by weight of the microemulsion;

wherein the microemulsion is prepared by the steps of:

(i) mixing the copolymer with an aqueous solution to dissolve the copolymer in the aqueous solution;

(ii) mixing the hydrophilic fatty acid emulsifier with a polyethoxylated side chain with the tea tree oil at a temperature from 15° C. to 40° C. to form an oil mixture; and (iii) mixing the copolymer solution prepared in step (i) with the mixture prepared in step (ii) at a temperature from 15° C. to 40° C. to form a microemulsion;

wherein (1) the tea tree oil is present in an effective amount to impart a pharmaceutical or cosmetic effect of the composition, (2) the microemulsion is thermoreversible and gelatinises or viscosifies upon contact with dermal, ophthalmic or mucosal tissue to develop bioadhesive or mucoadhesive properties and (3) the non-ionic block copolymer of ethylene oxide and propylene oxide is poloxamer 407.

* * * * *